(12) United States Patent
Konishi

(10) Patent No.: US 9,381,068 B2
(45) Date of Patent: Jul. 5, 2016

(54) SENSOR STORAGE CONTAINER

(71) Applicant: PANASONIC HEALTHCARE HOLDINGS CO., LTD., Minato-ku, Tokyo (JP)

(72) Inventor: Yuta Konishi, Ehime (JP)

(73) Assignee: PANASONIC HEALTHCARE HOLDINGS CO., LTD., Minato-Ku, Tokyo (JP)

( * ) Notice: Subject to any disclaimer, the term of this patent is extended or adjusted under 35 U.S.C. 154(b) by 199 days.

(21) Appl. No.: 14/355,576

(22) PCT Filed: Oct. 29, 2012

(86) PCT No.: PCT/JP2012/006906
§ 371 (c)(1),
(2) Date: Apr. 30, 2014

(87) PCT Pub. No.: WO2013/073117
PCT Pub. Date: May 23, 2013

(65) Prior Publication Data
US 2014/0311931 A1    Oct. 23, 2014

(30) Foreign Application Priority Data

Nov. 14, 2011  (JP) ................................. 2011-248337
Feb. 10, 2012  (JP) ................................. 2012-027267
Mar. 28, 2012  (JP) ................................. 2012-073197

(51) Int. Cl.
*B65D 83/10*        (2006.01)
*A61B 19/02*        (2006.01)
(Continued)

(52) U.S. Cl.
CPC ............ *A61B 19/026* (2013.01); *A61B 5/14532* (2013.01); *B65D 83/0835* (2013.01); *G01N 33/48757* (2013.01); *G01N 33/48778* (2013.01)

(58) Field of Classification Search
USPC ......... 206/363, 449, 305, 370, 804, 706, 710; 221/210, 33, 36, 37, 39
See application file for complete search history.

(56) References Cited

U.S. PATENT DOCUMENTS 3,094,323 A * 6/1963 Catania .................. A45D 2/127
                                                   221/210
5,322,190 A * 6/1994 Bartley .................. A47K 10/44
                                                   221/210

(Continued)

FOREIGN PATENT DOCUMENTS

JP    2006-188255 A    7/2006
JP    2007-084108 A    4/2007
(Continued)

OTHER PUBLICATIONS

International Search Report of Int'l Appln. No. PCT/JP2012/006906 issued on Dec. 11, 2012.

(Continued)

*Primary Examiner* — Jacob K Ackun
*Assistant Examiner* — Rafael Ortiz
(74) *Attorney, Agent, or Firm* — Shinjyu Global IP

(57) ABSTRACT

A sensor storage container includes: a lid configured to cover in an openable and closable manner an opening of an open-topped main body case that stores an elongated plate-like sensor lying flat; and a sensor ejecting tool configured to take the sensor out of the main body case. The sensor ejecting tool is elongated, and includes two ends, one end being linked to one of end sides of an opening portion of the main body case, and the other end being rotatable in a vertical direction between a bottom portion of the main body case and a position above the opening portion. A sensor adhesive portion at the other end of the sensor ejecting tool is provided with an adhesive face on a side of the sensor adhesive portion facing a bottom face of the main body case.

20 Claims, 7 Drawing Sheets

(51) Int. Cl.
*G01N 33/487* (2006.01)
*A61B 5/145* (2006.01)
*B65D 83/08* (2006.01)

(56) References Cited

U.S. PATENT DOCUMENTS

| | | | | |
|---|---|---|---|---|
| 2006/0191813 | A1* | 8/2006 | Yamaoka | C12Q 1/004 206/459.5 |
| 2006/0266758 | A1* | 11/2006 | Lewis | B65H 3/56 221/33 |
| 2006/0266759 | A1* | 11/2006 | Tramontina | A47K 10/423 221/33 |
| 2012/0080330 | A1* | 4/2012 | Rush | B65D 1/24 206/305 |

FOREIGN PATENT DOCUMENTS

| | | |
|---|---|---|
| JP | 2008-024312 A | 2/2008 |
| JP | 2008-37425 A | 2/2008 |
| JP | 2008-50037 A | 3/2008 |
| JP | 2009-023685 A | 2/2009 |
| JP | 2011-012996 A | 1/2011 |
| JP | 2011-117912 A | 6/2011 |
| JP | 4882565 B2 | 2/2012 |
| JP | 4949150 B2 | 6/2012 |

OTHER PUBLICATIONS

Notice of Allowance from the corresponding Japanese Patent Application No. 2013-544108 issued on May 19, 2015.

* cited by examiner

SENSOR STORAGE CONTAINER

PRIORITY

This is a continuation-in-part under 35 U.S.C. §120 and 35 U.S.C. §365 of International Application PCT/JP2012/006906, with an international filing date of Oct. 29, 2012, which claims priority to Japanese Patent Application No. 2011-248337 filed on Nov. 14, 2011, Japanese Patent Application No. 2012-027267 filed on Feb. 10, 2012, and Japanese Patent Application No. 2012-073197 filed on Mar. 28, 2012. The entire disclosures of International Application PCT/JP2012/006906, Japanese Patent Application No. 2011-248337, Japanese Patent Application No. 2012-027267, and Japanese Patent Application No. 2012-073197 are hereby incorporated herein by reference.

TECHNICAL FIELD

The present invention relates to a sensor storage container that stores a sensor for measuring the blood glucose level, for example.

BACKGROUND

A conventional sensor storage container is configured such that it includes: a main body case in the shape of a bottomed cylinder having an opening portion at the top, capable of storing a plurality of elongated plate-like sensors arranged upright; and a lid for covering the opening portion of the main body case in an openable/closable manner; wherein the main body case has an inclined bottom portion (see Patent Literature 1: JP 2011-117912A, for example).

When the main body case is turned on its side, the plurality of sensors are displaced relative to each other along the inclined bottom portion of the main body case. In this state, an attempt is made to take only the uppermost sensor out of the main body case from among the plurality of displaced sensors.

This conventional example is problematic in that it is difficult to take only one sensor out of the main body case.

In particular, according to the conventional example, when the main body case of the sensor storage container is turned on its side, the plurality of stacked sensors are displaced relative to each other along the inclined bottom portion of the main body case. In this state, an attempt is made to take only the uppermost sensor out of the main body case from among the plurality of displaced sensors.

When taking out the uppermost sensor, a user pulls this sensor out of the main body case while pressing the upper face of the sensor with a finger. At that time, a sensor disposed under the uppermost sensor is also pressed. Accordingly, the lower sensor is accidentally taken out as well due to friction between the sensors. As a result, it is often difficult to take only one sensor out of the main body case.

SUMMARY

The sensor storage container according to the present invention comprises: a main body case having an opening portion at a top of the main body case, the main body case being configured to store an elongated plate-like sensor lying flat; a lid configured to cover the opening portion of the main body case in an openable and closable manner; and a sensor ejecting tool for taking the sensor out of the main body case. The sensor ejecting tool is in an elongated shape and includes two ends, one end being linked to the opening portion of the main body case, and the other end being rotatable in a vertical direction with respect to the opening portion of the main body case. The other end of the sensor ejecting tool is provided with a sensor adhesive portion. The sensor adhesive portion is provided with an adhesive face on a side of the sensor adhesive portion facing a bottom face of the main body case.

As described above, the sensor storage container of the present invention is configured such that the sensor adhesive portion provided on the other end of the elongated sensor ejecting tool adheres to an uppermost sensor from among a stack of sensors lying flat and stored in the main body case. Accordingly, when the user rotates the sensor ejecting tool upward, only the uppermost sensor to which the sensor adhesive portion has adhered is lifted, and only one sensor can be taken out of the main body case.

DETAILED DESCRIPTION

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

First Embodiment

Hereinafter, a sensor storage container according to the first embodiment of the present invention will be described with reference to the drawings.

Figure 1:
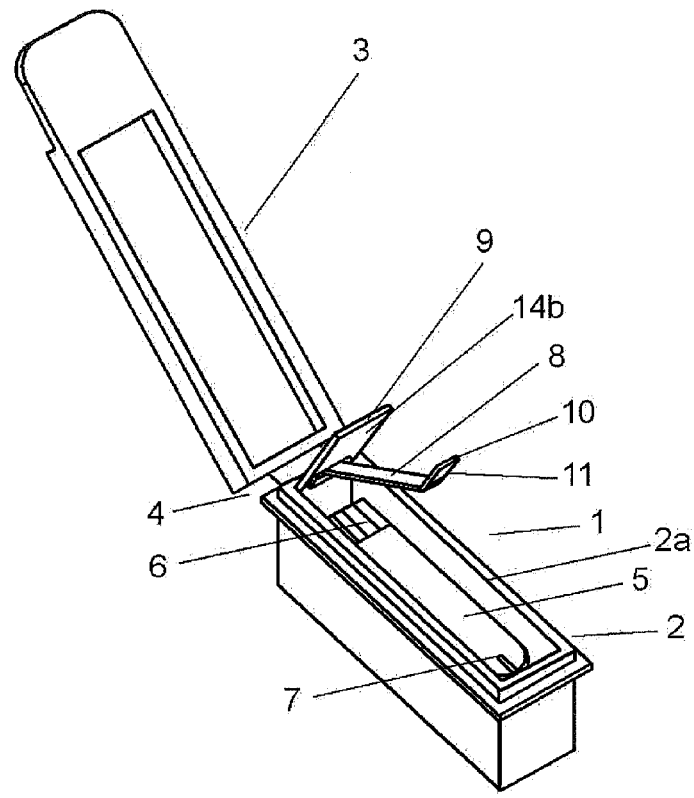
FIG. 1 is a perspective view of a sensor storage container according to a first embodiment of the present invention.

As shown in FIG. 1, a sensor storage container 1 includes a main body case 2 in the shape of a rectangular parallelepiped having a rectangular opening portion 2a at the top, and a lid 3 for covering the opening portion 2a of the main body case 2 in an openable and closable manner. The sensor storage container 1 is provided with, on one of the end sides at the top of the main body case 2, a link portion 4 that links the main body case 2 and the lid 3. The link portion 4 has a hinge configuration, and, thus, the lid 3 can be pivoted about the link portion 4 so as to open and close the main body case 2. Note that the main body case 2, the lid 3, and the link portion 4 are integrally molded from synthetic resin.

Figure 2:
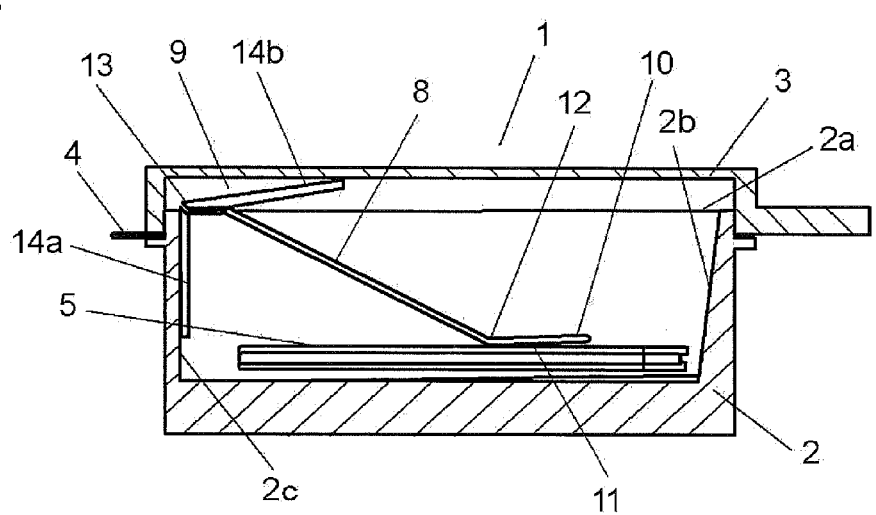
FIG. 2 is a cross-sectional view of the sensor storage container according to the first embodiment of the present invention.

As shown in FIG. 2, an inner wall 2b of the main body case 2 on the other end side not provided with the link portion 4 is inclined such that the top side of the main body case 2 is closer to the outside than the bottom face side of the main body case 2 is.

When the lid 3 is closed, the main body case 2 is sealed, and the internal portion of the sensor storage container 1 is kept dry by a desiccant contained in the bottom face and the side face of the main body case 2.

A plurality of elongated plate-like sensors 5 lying flat and stacked in one pile are stored in the main body case 2. The sensors 5 are for measuring the blood glucose level or the like, and each sensor has two ends, one of which is a connection terminal 6 that is to be connected to a measuring apparatus (not shown), and the other of which is a deposition portion 7 for deposition of the blood, as shown in FIG. 1. The sensors 5 are stored in the main body case 2 such that each deposition portion 7 is positioned on the inner wall 2b side of the main body case 2.

Figure 3:
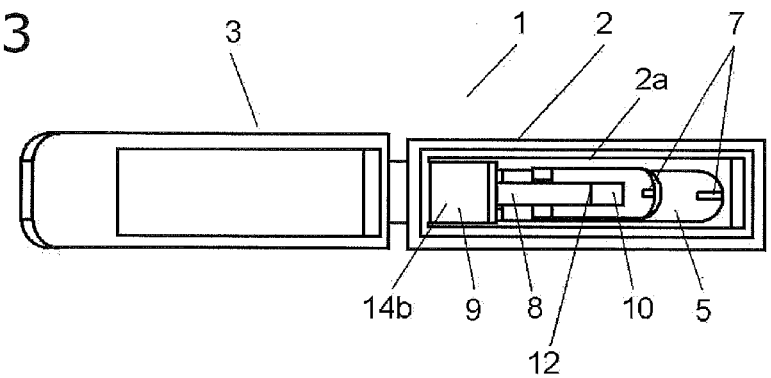
FIG. 3 is a top view of the sensor storage container according to the first embodiment of the present invention.

FIG. 3 is a top view of the sensor storage container 1 when the lid 3 is open. The length in the longitudinal direction of the internal portion of the main body case 2 is larger than the length in the longitudinal direction of the sensor 5 stored therein. Specifically, it is 1.3 times the length in the longitudinal direction of one sensor 5.

Moreover, the width in a direction orthogonal to the longitudinal direction of the internal portion of the main body case 2 is larger than the width in a direction orthogonal to the longitudinal direction of the sensor 5 and is smaller than twice the width thereof. More specifically, it is 1.5 times the width in a direction orthogonal to the longitudinal direction of the sensor 5.

Accordingly, the plurality of elongated plate-like sensors 5 lying flat and stacked in one pile are stored in the main body case 2.

As shown in FIGS. 1 and 2, a narrow elongated plate-like sensor ejecting tool 8 for taking the sensor 5 out of the main body case 2 is linked via a lift tool 9 to the one end side of the opening portion 2a of the main body case 2. The sensor ejecting tool 8 has the other end, which is not linked to the one end side of the opening portion 2a of the main body case 2 and is pivoted so as to be rotatable vertically between the bottom portion and a position above the opening portion 2a of the main body case 2. The other end of the sensor ejecting tool 8 is provided with a sensor adhesive portion 10 at a portion over a bent portion 12. The sensor adhesive portion 10 is provided with, on a side thereof facing the bottom face of the main body case 2, an adhesive face 11.

As shown in FIG. 3, the width, in a direction orthogonal to the longitudinal direction of the sensor ejecting tool 8, of the sensor adhesive portion 10 is smaller than the width in a direction orthogonal to the longitudinal direction of the sensor 5. Specifically, it is 0.5 times the width in a direction orthogonal to the longitudinal direction of the sensor 5.

Furthermore, as shown in FIG. 2, the length from one end to the other end of the sensor ejecting tool 8 is shorter than the length in the longitudinal direction of the sensor 5. Accordingly, the sensor adhesive portion 10 is brought into contact with the sensor 5 stored lying flat, substantially at the center thereof neither provided with the connection terminal 6 nor the deposition portion 7.

Note that the sensor ejecting tool 8 is formed by a flat plate-shaped elastic material, and, thus, the sensor adhesive portion 10 can be reliably brought into contact with the elongated plate-like sensor 5 using the elasticity of the sensor ejecting tool 8.

Note that the bent portion 12 is formed so as to lift the sensor adhesive portion 10 away from the bottom face of the main body case 2, and the portion extending from the bent portion 12 to the sensor adhesive portion 10 is rotatable in a vertical direction.

As shown in FIG. 2, the bent portion 12 is configured such that, when the elastic sensor ejecting tool 8 is rotated toward the bottom face of the main body case 2, the sensor adhesive portion 10 side of the sensor ejecting tool 8 applies a pressure toward the bottom face of the main body case 2. Accordingly, regardless of the number of sensors 5 stored, the sensor adhesive portion 10 can be properly brought into contact with the uppermost one of the sensors 5 stacked inside the main body case 2, using the elasticity of the sensor ejecting tool 8.

Next, the lift tool 9 that links the sensor ejecting tool 8 to the one end side of the opening portion 2a of the main body case 2 will be described.

The lift tool 9 is in the shape of an elastic flat plate, and a middle portion thereof is provided with a bent portion 13. The lift tool 9 is divided at the bent portion 13 into two portions, one of which is a fixing portion 14a that is bonded to an inner wall 2c on the one end side of the main body case 2 at a position near the opening portion 2a, and the other of which is a lift tab 14b that is bent inward inside the main body case 2.

The face of the lift tab 14b facing the bottom face of the main body case 2 is bonded to the sensor ejecting tool 8.

Accordingly, the lift tab 14b of the lift tool 9 is rotated about the bent portion 13 in a vertical direction, and, in conjunction with this rotation, the sensor adhesive portion 10 of the sensor ejecting tool 8 is rotated vertically between the bottom portion of the main body case 2 and a position above the opening portion 2a.

Note that the lift tab 14b is disposed above the opening portion 2a of the main body case 2. As shown in FIG. 1, when the lid 3 is open, the lift tab 14b is lifted greatly above the opening portion 2a of the main body case 2 due to the elasticity of the lift tool 9.

When the lid 3 is closed, the lift tab 14b of the lift tool 9 is pressed by the lid 3 and is bent at the bent portion 13 as shown in FIG. 2, so that the elastic lift tool 9 is stored in the sensor storage container 1 while holding pressure.

Hereinafter, a method for using the thus configured sensor storage container in this embodiment will be described.

First, a user opens the sensor storage container 1 as shown in FIG. 1, by pivotally moving the lid 3 of the sensor storage container 1 that has been closed by the lid 3 as shown in FIG. 2.

At that time, as the lid 3 is opened, the lift tool 9 that has been stored in the sensor storage container 1 while holding pressure is lifted above the opening portion 2a of the main body case 2 as shown in FIG. 1. At that time, the lift tab 14b of the lift tool 9 is lifted greatly above the opening portion 2a of the main body case 2. Moreover, the sensor ejecting tool 8 linked to the lift tool 9 is lifted above the opening portion 2a of the main body case 2 in conjunction with the movement of the lift tool 9.

Next, the user presses down the lifted lift tab 14b, for example, using an index finger. Then, the sensor ejecting tool 8 linked to the lift tab 14b is rotated downward, and the adhesive face 11 provided on the sensor adhesive portion 10 is pressed against the upper face of the uppermost sensor 5 from among the plurality of sensors 5 that are stacked and stored in the main body case 2.

Figure 4:
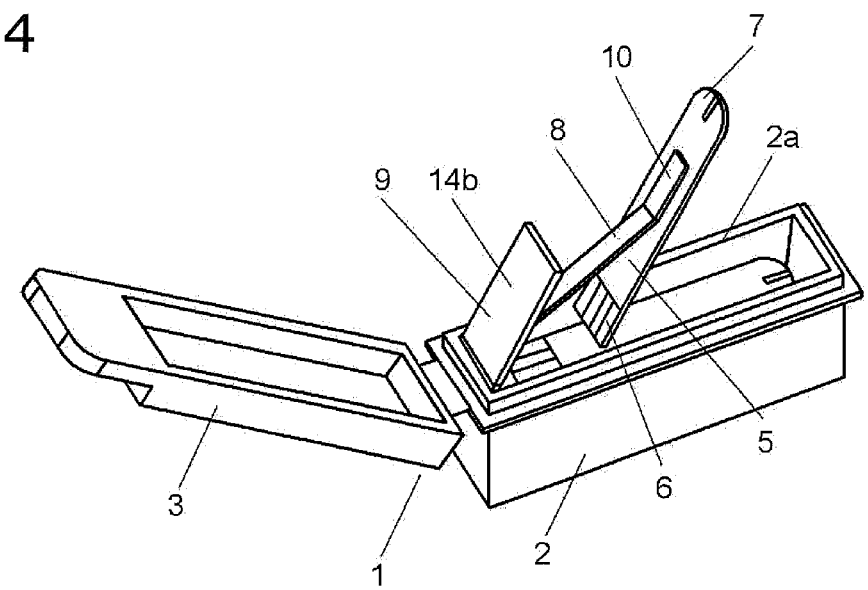
FIG. 4 is a perspective view of the sensor storage container according to the first embodiment of the present invention.

Accordingly, the adhesive face 11 adheres to the uppermost sensor 5. In this state, when the lift tab 14b is picked up, for example, between a thumb and an index finger and is rotated upward, the sensor ejecting tool 8 is rotated upward as shown in FIG. 4. Thus, only the uppermost sensor 5 to which the adhesive face 11 of the sensor adhesive portion 10 has adhered at a portion neither provided with the connection terminal 6 nor the deposition portion 7 is lifted out of the main body case 2, from among the plurality of stored sensors 5.

As shown in FIG. 2, the inner wall 2b on the other end side of the main body case 2 is inclined such that the top side of the main body case 2 is closer to the outside than the bottom face side of the main body case 2 is. With the inclined inner wall 2b on the other end side, the end portion of the lifted sensor 5 is not caught by the main body case 2, and only one sensor 5 can be taken out of the main body case 2.

Furthermore, at that time, as shown in FIGS. 3 and 4, the adhesive face 11 of the sensor ejecting tool 8 is in contact with neither the connection terminal 6 nor the deposition portion 7 of the sensor 5, and, thus, the adhesive face 11 of the sensor ejecting tool 8 does not affect measurement of the blood glucose level.

As a result, the sensor storage container 1 in this embodiment makes it possible to take only one sensor 5 out of the main body case 2 from among the plurality of stored sensors 5.

Second Embodiment

Figure 5:
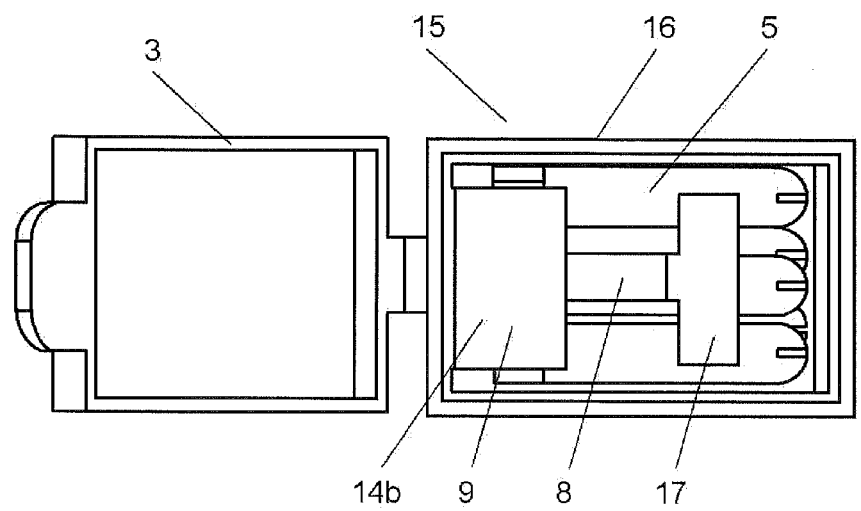
FIG. 5 is a top view of a sensor storage container according to a second embodiment of the present invention.
Figure 6:
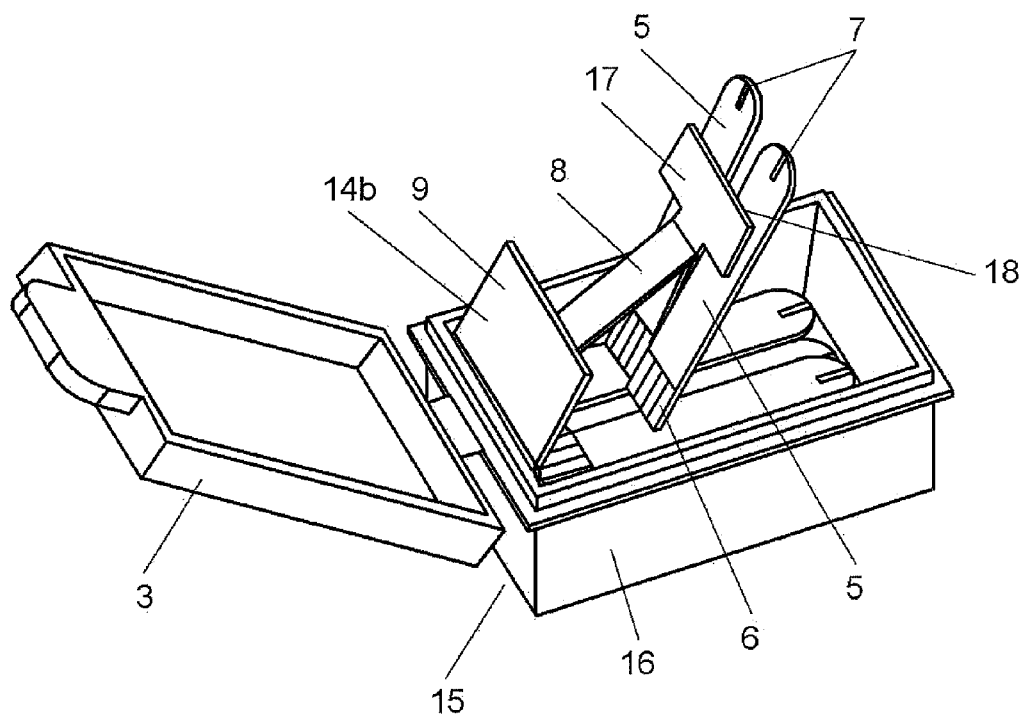
FIG. 6 is a perspective view of the sensor storage container according to the second embodiment of the present invention.

FIGS. 5 and 6 show a sensor storage container 15 according to the second embodiment of the present invention.

As shown in FIGS. 5 and 6, the sensor storage container 15 is formed such that it has a greater width in a direction orthogonal to a longitudinal direction of the sensor storage container than the sensor storage container 1 in the first embodiment and the sensors 5 stacked in a plurality of piles can be stored therein. More specifically, the sensor storage container 15 is configured such that the width in a direction orthogonal to the longitudinal direction of the internal portion of a main body case 16 is 3.5 times the width in a direction orthogonal to the longitudinal direction of each sensor 5.

Thus, a larger number of sensors 5 can be stored in the main body case 16.

In order to make it easy to take out the sensors 5 stored in a plurality of piles in this manner, in this embodiment, the width in a direction orthogonal to the longitudinal direction of the sensor ejecting tool 8, of a sensor adhesive portion 17 corresponding to the sensor adhesive portion 10 of the first embodiment, is larger than the width in a direction orthogonal to the longitudinal direction of the sensor 5. Specifically, it is 3 times the width in a direction orthogonal to the longitudinal direction of each sensor 5.

Note that, according to an increase in the size of the sensor adhesive portion 17, the size of an adhesive face 18 corresponding to the adhesive face 11 of the first embodiment is increased to be substantially the same as the size of the sensor adhesive portion 17.

When the lid 3 is open, the user presses down the lifted lift tab 14b of the lift tool 9, for example, using an index finger. Then, the adhesive face 18 of the sensor ejecting tool 8 linked to the lift tab 14b is simultaneously pressed against the upper faces of the plurality of uppermost sensors 5 from among the plurality of sensors 5 that are stacked in a plurality of piles and stored in the main body case 16.

Accordingly, the adhesive face 18 adheres to the plurality of uppermost sensors 5. In this state, when the lift tab 14b is picked up, for example, between a thumb and an index finger and is rotated upward, the plurality of sensors 5 are lifted out of the main body case 16 as shown in FIG. 6.

The user can select and eject one sensor 5 that can be most easily taken out, from among the plurality of lifted sensors 5.

As a result, the sensor storage container 15 in this embodiment makes it possible to take only one sensor 5 out of the main body case 16.

Third Embodiment

Figure 7:
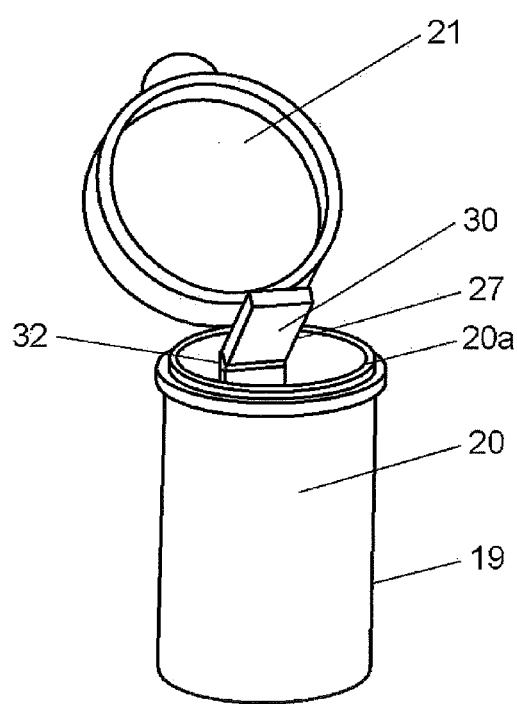
FIG. 7 is a perspective view of a sensor ejecting tool and a sensor storage container according to a third embodiment of the present invention.
Figure 8:
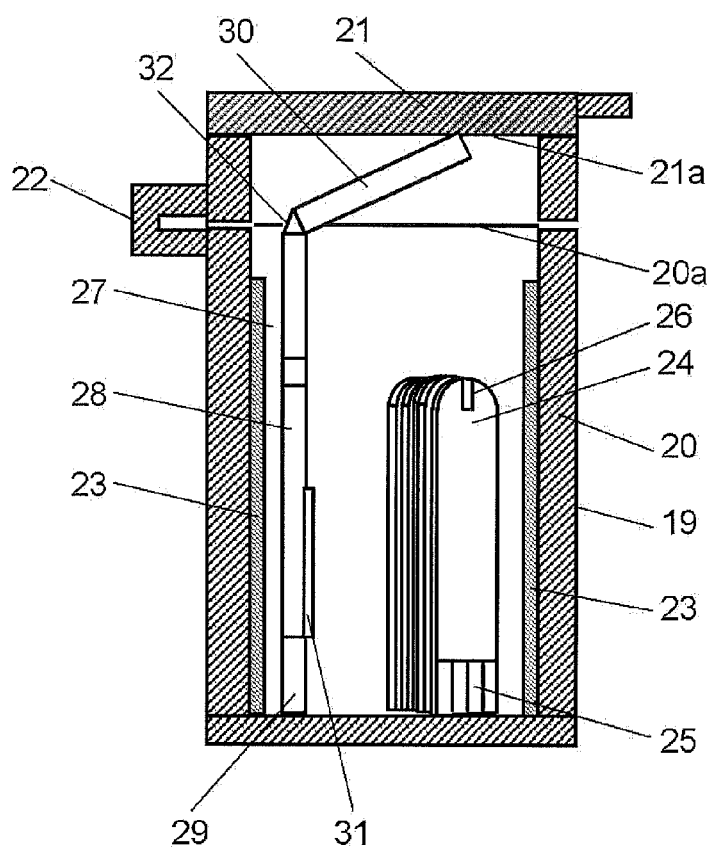
FIG. 8 is a cross-sectional view of the sensor ejecting tool and the sensor storage container according to the third embodiment of the present invention.

As shown in FIGS. 7 and 8, in the third embodiment of the present invention, sensors 24 are stored in a sensor storage container 19 in the shape of a cylinder. With the sensor storage container 19, it is possible to easily take only one sensor 24 out of the sensor storage container 19.

Hereinafter, the third embodiment of the present invention will be described with reference to the drawings.

As shown in FIG. 7, the sensor storage container 19 includes a container 20 in the shape of a bottomed cylinder having an opening portion 20a at the top, and a lid member 21 provided at the upper edge of the container 20. Furthermore, as shown in FIG. 8, the sensor storage container 19 includes a link portion 22 that links the container 20 and the lid member 21. The link portion 22 has a hinge configuration, and, thus, the lid member 21 can be rotated about the link portion 22 so as to open and close the opening portion 20a at the top of the container 20. Note that the container 20, the lid member 21, and the link portion 22 are integrally molded from synthetic resin.

A desiccant layer 23 in the shape of an open-topped cylinder is unitarily provided on the inner face of the container 20, extending from the upper portion to the lower portion thereof. The desiccant layer 23 is made of soft resin containing a desiccant.

In this state, the plurality of elongated plate-like sensors 24 for measuring the blood glucose level or the like are stored upright in the container 20, specifically, in the portion surrounded by the desiccant layer 23.

The sensors 24 for measuring the blood glucose level each have two ends, one of which is a connection terminal 25 (lower end in FIG. 8) that is to be inserted to a measuring apparatus (not shown), and the other of which is a deposition portion 26 (upper end in FIG. 8) for deposition of the blood.

The length in the longitudinal direction of the sensor 24 is larger than the diameter of the container 20, and the depth of the container 20, which is the length in the cylindrical axis direction of the container 20, is larger than the length of the sensor 24. Accordingly, the sensors 24 do not fall inside the container 20 and are not turned upside down, and the sensors 24 are stored in the container 20 such that they stand on the bottom face of the container 20 with the connection terminals 25 being positioned on the lower side as shown in FIG. 8.

The user carries around the container 20 in which the plurality of sensors 24 are stored, and takes one sensor 24 out of the container 20 for use in the measurement of the blood glucose level.

In order to make it easy to take out the sensor 24, in the third embodiment of the present invention, a sensor ejecting tool 27 is inserted into the container 20 as shown in FIGS. 7 and 8.

Figure 9:
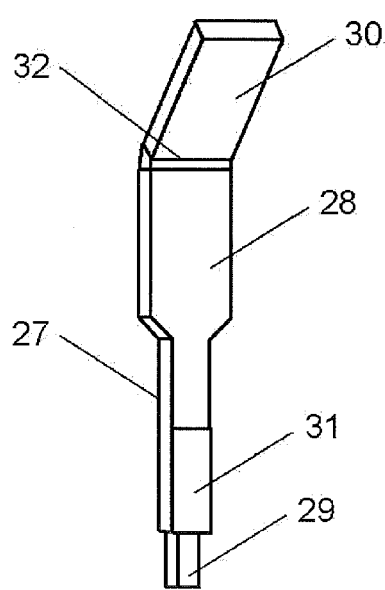
FIG. 9 is a perspective view of the sensor ejecting tool according to the third embodiment of the present invention.

As shown in FIG. 9, the sensor ejecting tool 27 includes a narrow elongated plate-like ejecting tool main body 28, a non-adhesive portion 29 provided at the lower end shown in FIG. 9 of the ejecting tool main body 28, and a tab portion 30 provided at the upper end (in FIG. 9) of the ejecting tool main body 28.

Furthermore, an adhesive portion 31 is provided on the surface of the ejecting tool main body 28 at a portion that is closer to the tab portion 30 than the non-adhesive portion 29 at the lower end is.

Moreover, a bent portion 32 is formed in a direction orthogonal to the longitudinal direction of the ejecting tool main body 28, at a position away by a predetermined distance from the upper end of the ejecting tool main body 28 toward the adhesive portion 31. The portion from the bent portion 32 to the upper end is bent to form the tab portion 30.

The adhesive portion 31 is provided on the surface of the ejecting tool main body 28 facing a direction in which the tab portion 30 is inclined.

The ejecting tool main body 28 is made of synthetic resin (an example of elastic material), and is in the shape of a thin plate.

The size, in a direction orthogonal to the longitudinal direction of the ejecting tool main body 28, of the non-adhesive portion 29 provided at the lower end of the ejecting tool main body 28, that is, the size in the width direction corresponding to the left-right direction in FIG. 9 (hereinafter, referred to as the size in the width direction) is smaller than the size in the longitudinal direction of the non-adhesive portion 29.

Furthermore, the size in the width direction of the adhesive portion 31 that is closer to the tab portion 30 than the non-adhesive portion 29 is, is larger than the size in the width direction of the non-adhesive portion 29.

Moreover, the size in the width direction of the tab portion 30 is larger than the size in the width direction of the adhesive portion 31.

That is to say, the tab portion 30 has the largest size in the width direction, followed in order by the adhesive portion 31 and the non-adhesive portion 29.

Furthermore, as shown in FIG. 8, the size in the longitudinal direction of the non-adhesive portion 29 is larger than the size in the longitudinal direction of the connection terminal 25 provided in the sensor 24.

As shown in FIG. 8, the container 20 stores the plurality of sensors 24 with the connection terminals 25 being positioned on the lower side, and further stores the sensor ejecting tool 27 with the non-adhesive portion 29 being positioned on the lower side. Subsequently, the lid member 21 seals the container 20 by closing the opening portion 20a thereof.

At that time, the size from the lower end to the bent portion 32 of the sensor ejecting tool 27 is the same as or lower than the height of the container 20. As shown in FIG. 8, in this embodiment, the size from the lower end to the bent portion 32 of the sensor ejecting tool 27 is substantially the same as the height of the container 20.

With this configuration, the upper end of the tab portion 30 above the bent portion 32 of the sensor ejecting tool 27 is positioned above the highest point of the container 20.

Accordingly, as shown in FIG. 7, when the lid member 21 is open, the tab portion 30 emerges above the opening portion 20a of the container 20, and, thus, the user can easily pick up the tab portion 30.

Furthermore, as shown in FIG. 8, the lid member 21 is in the shape of a bottomed cylinder having the opening portion 20a facing the container 20. When the lid member 21 closes the container 20, an inner bottom face 21a of the lid member 21 is brought into contact with the upper end portion of the tab portion 30 of the sensor ejecting tool 27, and presses down the tab portion 30 at the bent portion 32. Since the sensor ejecting tool 27 is formed by an elastic material, the tab portion 30 is bent inside the lid member 21 while holding pressure.

Hereinafter, a method for using the thus configured sensor ejecting tool 27 in this embodiment will be described. First, a user opens the container 20 as shown in FIG. 7, by pivotally moving the lid member 21 of the container 20 that has been closed by the lid member 21 as shown in FIG. 8.

At that time, since the tab portion 30 of the sensor ejecting tool 27 has been bent while holding pressure as described above, when the container 20 is opened, the tab portion 30 is released and lifted upward. Accordingly, the user can easily pick up the tab portion 30 at a position above the container 20, for example, using a thumb and an index finger.

Figure 10:
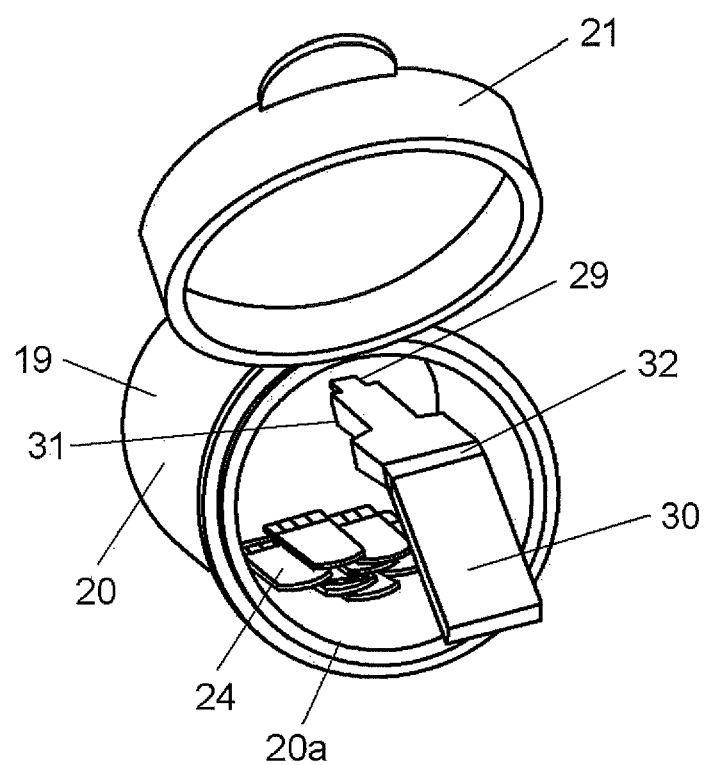
FIG. 10 is a perspective view of the sensor ejecting tool and the sensor storage container according to the third embodiment of the present invention viewed from above.

Next, as shown in FIG. 10, the user tilts the container 20 such that the opening portion 20a of the container 20 faces the user. Accordingly, the sensors 24 are stacked on the side toward which the container 20 has been tilted (lower side in FIG. 10), from the bottom face along the inner wall face of the container 20.

As described above, the tab portion 30 has the largest size in the width direction, followed in order by the adhesive portion 31 and the non-adhesive portion 29. Accordingly, even when the ejecting tool main body 28 is inserted into the container 20, the state of the sensors 24 stacked on the bottom face of the container 20 can be easily seen.

Subsequently, the user finds the sensor 24 that can be most easily taken out, and presses the adhesive portion 31 against that targeted sensor 24 by operating the tab portion 30. Since the sensor ejecting tool 27 is formed by an elastic material, the ejecting tool main body 28 is slightly warped, and the adhesive portion 31 can be pressed against the upper face of the targeted sensor 24 with a proper pressure.

Furthermore, in this embodiment, the size in the longitudinal direction of the non-adhesive portion 29 provided in the lower portion of the sensor ejecting tool 27 is larger than the size in the longitudinal direction of the connection terminal 25 provided in the lower portion of the sensor 24. Accordingly, the adhesive portion 31 does not adhere to the connection terminal 25.

Moreover, the size in the width direction of the non-adhesive portion 29 is smaller than that of the adhesive portion 31. Accordingly, a stepped portion is formed at the link portion between the non-adhesive portion 29 and the adhesive portion 31, and, thus, the user can easily know the position of the adhesive portion 31 even inside the container 20.

Moreover, the size in the width direction of the adhesive portion 31 is substantially the same as the size in a direction orthogonal to the longitudinal direction of the sensor 24. Accordingly, the adhesive portion 31 can adhere to only one sensor 24.

Moreover, the adhesive portion 31 is provided only on the side of the ejecting tool main body 28 facing in a direction in which the tab portion 30 is inclined, and is not provided on the opposite side. That is to say, the adhesive portion 31 is provided only on one of the sides of the ejecting tool main body 28. Accordingly, the adhesive portion 31 does not adhere to two sensors 24.

Subsequently, when the user operates the tab portion 30 in the state where the adhesive portion 31 has adhered to the sensor 24, only one sensor 24 to which the adhesive portion 31 has adhered can be lifted.

Figure 11:
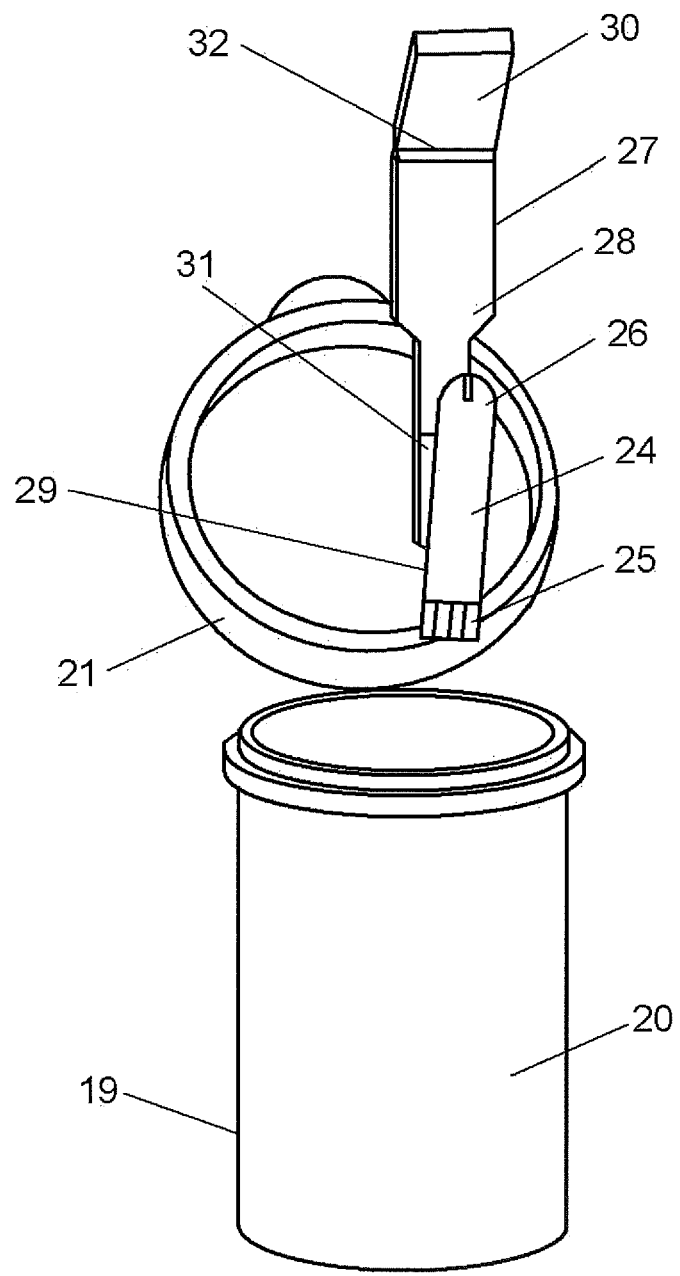
FIG. 11 is a perspective view of the sensor ejecting tool and the sensor storage container according to the third embodiment of the present invention.

Lastly, when the ejecting tool main body 28 is pulled out of the container 20, one sensor 24 to which the adhesive portion 31 has adhered emerges as shown in FIG. 11.

As a result, only one sensor 24 can be taken out of the container 20.

Note that, although the sensor ejecting tool 27 was stored in the container 20 in this embodiment, the container 20 and the sensor ejecting tool 27 may be separately carried around, and the sensor ejecting tool 27 may be used when taking out the sensor 24.

At that time, only one sensor 24 to which the adhesive portion 31 has adhered can be taken out of the container 20, by inserting the ejecting tool main body 28 from its non-adhesive portion 29 side into the container 20.

As described above, the sensor ejecting tool 27 of this embodiment includes the elongated ejecting tool main body 28, the non-adhesive portion 29 provided at one of the ends of the ejecting tool main body 28, and the tab portion 30 provided at the other end of the ejecting tool main body 28. Furthermore, the adhesive portion 31 is provided on the ejecting tool main body 28 at a portion that is closer to the tab portion 30 than the non-adhesive portion 29 is. This configuration makes it possible to take only one sensor 24 out of the container 20 of the sensor storage container 19.

That is to say, the sensor ejecting tool 27 of this embodiment is configured such that the adhesive portion 31 is provided on the ejecting tool main body 28 at a portion that is closer to the tab portion 30 than the non-adhesive portion 29 is. With this configuration, when the sensor 24 is taken out of the sensor storage container 19, the sensor 24 to which the adhesive portion 31 has adhered can be lifted, by inserting the ejecting tool main body 28 from its non-adhesive portion 29 side into the sensor storage container 19. Thus, only one sensor 24 that has been lifted can be easily taken out of the sensor storage container 19.

Fourth Embodiment

Figure 12:
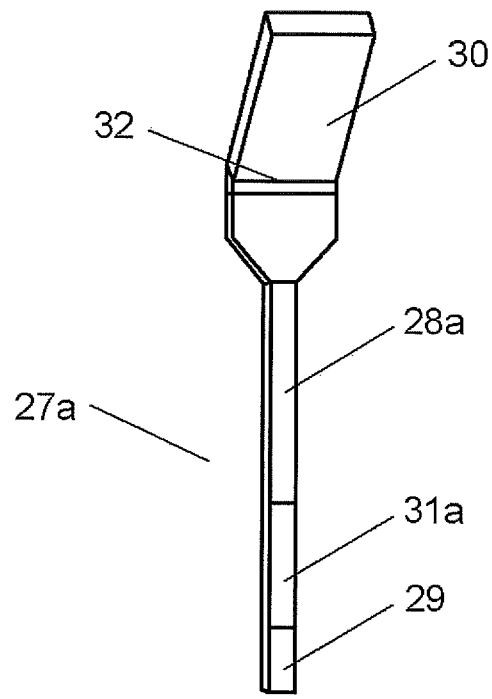
FIG. 12 is a perspective view of a sensor ejecting tool according to a fourth embodiment of the present invention.

FIG. 12 shows a sensor ejecting tool 27a according to the fourth embodiment of the present invention. As shown in FIG. 12, the sensor ejecting tool 27a is formed by shaping the ejecting tool main body 28 of the sensor ejecting tool 27 in the third embodiment into the shape of an elongated bar. More specifically, a portion from the middle of an ejecting tool main body 28a to the non-adhesive portion 29 at the lower end is formed in the shape of a bar having a quadrangular cross-section.

That is to say, in this embodiment, the portion from the middle to the lower end of the ejecting tool main body 28a is formed in a narrow shape. More specifically, for example, the width of the portion from the middle to the lower end of the ejecting tool main body 28a is 0.25 times the width of one sensor 24.

Accordingly, when the user inserts the ejecting tool main body 28a into the container 20, the state of the sensors 24 stacked on the bottom face of the container 20 can be more easily seen because the ejecting tool main body 28a is narrow. Thus, the user can easily bring an adhesive portion 31a into contact with the sensor 24.

Subsequently, the user lifts the sensor 24 to which the adhesive portion 31a of the ejecting tool main body 28a has adhered. In this state, the ejecting tool main body 28a is pulled out of the container 20, and the sensor 24 is detached from the adhesive portion 31a. Also at that time, the ejecting tool main body 28a does not make it difficult to detach the sensor 24 because the ejecting tool main body 28a is narrow, and the user can reliably pick up the sensor 24 with fingers. Thus, the sensor 24 can be easily detached from the adhesive portion 31a of the ejecting tool main body 28a.

As a result, the ease of use is improved also when detaching the sensor 24.

Fifth Embodiment

Figure 13:
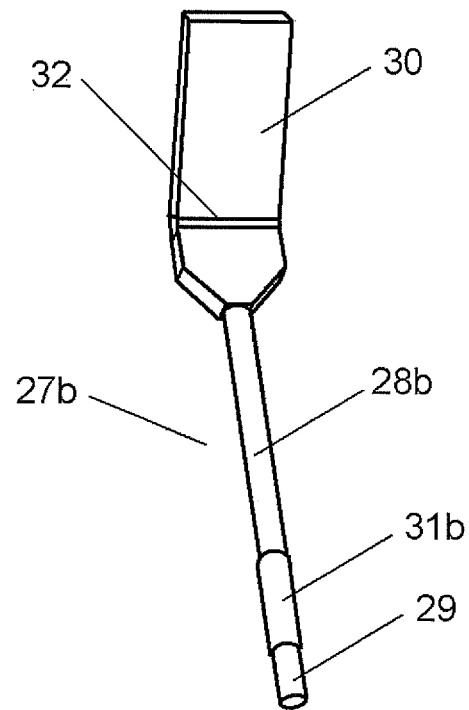
FIG. 13 is a perspective view of a sensor ejecting tool according to a fifth embodiment of the present invention.

FIG. 13 shows a sensor ejecting tool 27b according to the fifth embodiment of the present invention. As shown in FIG. 13, the sensor ejecting tool 27b is formed by shaping the ejecting tool main body 28a of the sensor ejecting tool 27a in the fourth embodiment into the shape of an elongated circular column.

Accordingly, an adhesive portion 31b provided on an ejecting tool main body 28b is formed as a curved face. Thus, the user may bring the adhesive portion 31b into contact, at any position of the curved face, with the sensor 24. As a result, the ease of use is improved.

Moreover, the adhesive portion 31b formed on the surface of the ejecting tool main body 28b is formed throughout the circumference of the circular column. Accordingly, the area that can be brought into contact with the sensor 24 increases, and therefore, the curved face of the adhesive portion 31b can be easily brought into contact with the sensor 24.

Note that, although the ejecting tool main body 28b was formed in the shape of a circular column having a circular cross-section in this embodiment, it may be formed in the shape of a column having an elliptical cross-section.

Furthermore, also in the fourth embodiment 4 and the fifth embodiment, the size from the lower end to the bent portion 32 of the sensor ejecting tool 27a or the sensor ejecting tool 27b is the same as or lower than the height of the container 20 in FIG. 7 for example. Specifically, in the fourth embodiment and the fifth embodiment, the size from the lower end to the bent portion 32 of the sensor ejecting tool 27a or the sensor ejecting tool 27b is substantially the same as the height of the container 20.

With this configuration, the upper end of the tab portion 30 above the bent portion 32 of the sensor ejecting tool 27a or the sensor ejecting tool 27b is positioned above the highest point of the container 20.

Accordingly, as shown in FIG. 7, when the lid member 21 is open, the tab portion 30 of the sensor ejecting tool 27a or the sensor ejecting tool 27b emerges above the opening portion 20a of the container 20, and, thus, the user can easily pick up the tab portion 30.

As described above, the sensor storage container of the present invention includes: a lid configured to cover in an openable and closable manner an opening portion of an open-topped main body case that stores an elongated plate-like sensor lying flat; and a sensor ejecting tool configured to take the sensor out of the main body case. The sensor ejecting tool is in an elongated shape, and has two ends, one end being linked to the opening portion of the main body case, and the other end being rotatable in a vertical direction with respect to the opening portion of the main body case. The other end of the sensor ejecting tool is provided with a sensor adhesive portion. The sensor adhesive portion is provided with an adhesive face on a side of the sensor adhesive portion facing a bottom face of the main body case. The thus configured sensor storage container of the present invention makes it possible to easily take out only one sensor.

That is to say, the sensor storage container of the present invention is configured such that the sensor adhesive portion provided on the other end of the elongated sensor ejecting tool adheres to the uppermost sensor from among the sensors stacked lying flat and stored in the main body case. Accordingly, when the user rotates the sensor ejecting tool upward, only the uppermost sensor to which the sensor adhesive portion has adhered is lifted.

As a result, only one sensor can be taken out of the main body case.

INDUSTRIAL APPLICABILITY

It is expected that the present invention can be widely applied to a sensor ejecting tool and a sensor storage container that stores the sensor ejecting tool.

The invention claimed is:

1. A sensor storage container, comprising:
   a main body case including an opening portion, a bottom portion, and a bottom face;
   the opening portion disposed at a top of the main body case and including a plurality of end sides;
   a sensor having an elongated plate-like shape stored lying flat inside of the main body case;
   a lid covering the opening portion of the main body case, the lid configured to open and close; and
   a sensor ejecting tool configured to eject the sensor from the main body case,
   the sensor ejecting tool having an elongated shape,
   the sensor ejecting tool and including a first end and a second end;
   the first end linked to an end side of the opening portion of the main body case;
   the second end rotatable in a vertical direction between the bottom portion of the main body case and a position above the opening portion of the main body case; and
   a sensor adhesive portion disposed at the second end, the sensor adhesive portion including an adhesive face disposed on a side of the sensor adhesive portion that faces the bottom face of the main body case.

2. The sensor storage container according to claim 1, wherein:
   the sensor further includes a first end and a second end;
   a first length from the first end to the second end of the sensor ejecting tool is shorter than a second length from the first end to the second end of the sensor.

3. The sensor storage container according to claim 1, wherein:
   the sensor adhesive portion is formed substantially in a flat plate shape.

4. The sensor storage container according to claim 1, wherein:
   the sensor ejecting tool is substantially composed of an elastic material.

5. The sensor storage container according to claim 4, wherein:
   the sensor ejecting tool further includes a bent portion configured to lift the sensor adhesive portion away from the bottom face of the main body case,
   the bent portion is disposed at a portion of the sensor ejecting tool that is closer to the first end of the sensor ejecting tool than the sensor adhesive portion, and
   a portion of the sensor ejecting tool, from the bent portion to the sensor adhesive portion, is rotatable in the vertical direction.

6. The sensor storage container according to claim 1, wherein:
   the main body case further includes a lift tool and an inner wall,
   the lift tool is configured to lift the sensor ejecting tool,
   the inner wall is disposed on the first end side of the main body case,
   the lift tool further includes a lift tab,
   the lift tab includes a first end and a second end,
   the first end of the lift tab is bonded to the inner wall of the main body case at the opening portion,
   the second end of the lift tab projects away from the first end of the lift tab, and
   the lift tab is attached to the sensor ejecting tool.

7. The sensor storage container according to claim 6, wherein:
   the lift tab is disposed above the opening portion of the main body case.

8. The sensor storage container according to claim 1, wherein:
   an inner wall on the other one of the end sides of the main body case is inclined such that the opening portion side is positioned closer to the outside than the bottom face side is.

9. The sensor storage container according to claim 1, wherein:
   the sensor further includes a connection portion at one end of the sensor, and a deposition portion at an opposite end of the sensor, and
   the sensor is stored in the main body case such that the deposition portion is positioned on the second end side of the main body case.

10. The sensor storage container according to claim 1, wherein:
    the sensor adhesive portion further includes a width in a direction orthogonal to a longitudinal direction of the sensor ejecting tool, and
    the width of the sensor adhesive portion is smaller than a width of the sensor in a direction orthogonal to a longitudinal direction of the sensor.

11. The sensor storage container according to claim 1, wherein:
    the sensor adhesive portion further includes a width in a direction orthogonal to a longitudinal direction of the sensor ejecting tool, and
    the width of the sensor adhesive portion is larger than a width of the sensor in a direction orthogonal to a longitudinal direction of the sensor.

12. The sensor storage container according to claim 2, wherein:
    the sensor adhesive portion is formed substantially in a flat plate shape.

13. The sensor storage container according to claim 2, wherein:
    the sensor ejecting tool is substantially composed of an elastic material.

14. The sensor storage container according to claim 13, wherein:
    the sensor ejecting tool further includes a bent portion configured to lift the sensor adhesive portion away from the bottom face of the main body case,
    the bent portion is disposed at a portion of the sensor ejecting tool that is closer to the first end of the sensor ejecting tool than the sensor adhesive portion, and
    a portion of the sensor ejecting tool, from the bent portion to the sensor adhesive portion, is rotatable in the vertical direction.

15. The sensor storage container according to claim 2, wherein:
    the main body case further includes a lift tool and an inner wall,
    the lift tool is configured to lift the sensor ejecting tool,
    the inner wall is disposed on the first end side of the main body case,
    the lift tool further includes a lift tab,
    the lift tab includes a first end and a second end,
    the first end of the lift tab is bonded to the inner wall of the main body case at the opening portion,
    the second end of the lift tab projects away from the first end of the lift tab, and
    the lift tab is attached to the sensor ejecting tool.

16. The sensor storage container according to claim 15, wherein:
    the lift tab is disposed above the opening portion of the main body case.

17. The sensor storage container according to claim 2, wherein:
   an inner wall on the other one of the end sides of the main body case is inclined such that the opening portion side is positioned closer to the outside than the bottom face side is.

18. The sensor storage container according to claim 2, wherein:
   the sensor further includes a connection portion at one end of the sensor, and a deposition portion at an opposite end of the sensor, and
   the sensor is stored in the main body case such that the deposition portion is positioned on the second end side of the main body case.

19. The sensor storage container according to claim 2, wherein:
   the sensor adhesive portion further includes a width in a direction orthogonal to a longitudinal direction of the sensor ejecting tool, and
   the width of the sensor adhesive portion is smaller than a width of the sensor in a direction orthogonal to a longitudinal direction of the sensor.

20. The sensor storage container according to claim 2, wherein:
   the sensor adhesive portion further includes a width in a direction orthogonal to a longitudinal direction of the sensor ejecting tool, and
   the width of the sensor adhesive portion is larger than a width of the sensor in a direction orthogonal to a longitudinal direction of the sensor.

* * * * *